US006539784B1

(12) United States Patent
King et al.

(10) Patent No.: US 6,539,784 B1
(45) Date of Patent: Apr. 1, 2003

(54) EVALUATION OF A MOTOR VEHICLE OXYGEN SENSOR PERFORMANCE

(75) Inventors: Paul John King, Loughborough (GB); Timothy John Kennedy, Daventry (GB)

(73) Assignee: Ford Global Technologies, Inc., Dearborn, MI (US)

( * ) Notice: Subject to any disclaimer, the term of this patent is extended or adjusted under 35 U.S.C. 154(b) by 75 days.

(21) Appl. No.: 09/614,102

(22) Filed: Jul. 12, 2000

(30) Foreign Application Priority Data

Jul. 12, 1999 (GB) ........................................... 9916163

(51) Int. Cl.[7] ...................... G01M 19/00; G01N 33/497

(52) U.S. Cl. ..................................... 73/118.1; 73/23.31

(58) Field of Search ............................... 73/118.1, 116, 73/23.31, 23.32; 123/688, 479, 691; 60/276, 277; 701/109

(56) References Cited

U.S. PATENT DOCUMENTS

| | | | | |
|---|---|---|---|---|
| 4,825,683 A | * | 5/1989 | Takami et al. | 73/1 G |
| 5,235,957 A | | 8/1993 | Furuya | 123/688 |
| 5,423,203 A | | 6/1995 | Namiki et al. | 73/1 G |
| 5,672,817 A | | 9/1997 | Sagisaka et al. | 73/118.1 |
| 5,685,284 A | * | 11/1997 | Nakamichi | 123/688 |
| 5,929,320 A | * | 7/1999 | Yoo | 73/23.31 |

FOREIGN PATENT DOCUMENTS

DE 19722334 A1 5/1997

* cited by examiner

*Primary Examiner*—Eric S. McCall
*Assistant Examiner*—Maurice Stevens
(74) *Attorney, Agent, or Firm*—Julia Voutyras; Allan J. Lippa

(57) ABSTRACT

The invention relates to the performance evaluation of an oxygen gas sensor in a motor vehicle, where the oxygen gas sensor is used to measure the oxygen content of the combusted air fuel mixture of a motor vehicle exhaust. The method involves measuring the fall time for the detected oxygen level to fall to a pre-determined lower threshold after the fuel supply to the engine has been cut off, and if the measured fall time exceeds a pre-set time, producing an oxygen sensor degradation signal.

18 Claims, 2 Drawing Sheets

EVALUATION OF A MOTOR VEHICLE OXYGEN SENSOR PERFORMANCE

FIELD OF THE INVENTION

This invention relates to the evaluation of an oxygen gas sensor performance in a motor vehicle. More particularly, the invention relates to diagnosing sensor performance degradation based on increased response time.

BACKGROUND OF THE INVENTION

In order to improve the efficiency of an internal combustion engine in a motor vehicle, an oxygen sensor is often used to sense the oxygen content of the exhaust gas, and the air-fuel mixture admitted to the engine is adjusted by the engine management system according to the sensed oxygen level of the exhaust gas.

As the oxygen sensor deteriorates with age, the response time of the oxygen sensor can increase, leading to a less than optimal air-fuel mixture and to reduced engine efficiency. A known method of monitoring the efficacy of the oxygen sensor involves measuring the response of the oxygen sensor when the amount of fuel admitted to the engine is forcibly changed during feedback control, as disclosed in U.S. Pat. No. 5,685,284. The inventors herein have recognised a disadvantage with the above approach. This method is complicated and requires an increased degree of accuracy in the control of the fuel supply.

SUMMARY OF THE INVENTION

An object of the present invention is to provide an improved method for evaluating performance of an oxygen sensor.

The above object is achieved and disadvantages of prior approaches overcome by a performance evaluation method for an oxygen sensor that detects an oxygen concentration level in an exhaust gas from an internal combustion engine. The method includes the steps of: cutting off a fuel supply to the internal combustion engine and allowing the detected oxygen concentration level of the exhaust gas to rise; reinstating said fuel supply after the detected oxygen concentration level has risen above a pre-determined upper threshold; measuring a fall time for the detected oxygen concentration level to fall to a pre-determined lower threshold from the moment the fuel supply is reinstated; and producing an oxygen sensor degradation signal if the measured fall time exceeds a pre-set time.

According to a second aspect of the present invention, there is provided an oxygen sensor performance evaluating system that detects an oxygen concentration level of an exhaust gas of an internal combustion engine. The system includes: means for cutting off a fuel supply to the internal combustion engine and allowing the detected oxygen concentration level of the exhaust gas to rise; means for reinstating a fuel supply after the detected oxygen concentration level has risen above a pre-determined upper threshold; means for measuring a fall time from the moment the fuel supply is reinstated for the detected oxygen concentration level to fall to a pre-determined lower threshold; and means for producing an oxygen sensor degradation signal if the measured fall time exceeds a pre-set time.

According to a third aspect of the present invention, there is provided a performance evaluating system for an oxygen sensor that detects an oxygen concentration level of an exhaust gas of an internal combustion engine with an engine management system. The system includes: a microprocessor having a counter-timer and being adapted to receive signals from the engine management system and the oxygen sensor, wherein if the microprocessor receives a command signal from the engine management system indicating that fuel to the engine has been cut off, followed by a signal from the oxygen sensor indicating that the detected oxygen concentration level has reached an upper threshold, the microprocessor is adapted to measure an elapsed time from the moment the engine management system issues a command for fuel reinstatement until the detected oxygen concentration level has fallen to a lower threshold value, and if the elapsed time is greater than a pre-set time, to issue an oxygen sensor degradation signal.

An advantage of the above aspects of the invention is that since feedback control of the fuel supply is not required, the accuracy in the control of the fuel supply is not important in determining whether the oxygen sensor performance is degraded. The upper threshold in the oxygen content after which fuel is reinstated need not be sensed, and may therefore be assumed to have been reached after a pre determined time interval after fuel cut off has occurred, but preferably the oxygen sensor is used to determined when the upper threshold has been reached.

The upper threshold may be the oxygen concentration at which the oxygen sensor saturates, and the lower threshold will typically be fixed at a value between 70% and 85% of the upper threshold oxygen concentration.

However, the lower threshold may be varied as a function of the reinstated fuel level in order to take into account any effect of the reinstated fuel level on the actual oxygen content in the exhaust.

After the upper threshold has been reached, the fuel may be reinstated by the engine management system when the accelerator pedal is depressed, or alternatively the fuel may be reinstated just before the engine speed has dropped to a low enough value for the engine to stall, so that in either case the failure determination method does not interfere with the fuelling of the engine.

To provide reproducible starting conditions, the fall time for the sensed oxygen content to reach the lower threshold may be measured from the moment the engine management system issues a command signal for fuel reinstatement.

The engine management system may provide a command signal for fuel reinstatement that comprises a single step, so that fuel reinstatement is as abrupt as possible.

The fall time may conveniently be measured by a counter-timer that is set to run by a microprocessor when the microprocessor senses the negative edge of the command signal for fuel reinstatement issued by the engine management system.

The counter-timer may be re-set to zero by the microprocessor after the lower threshold has been reached, but preferably the counter-timer will be re-set before fuel reinstatement.

The pre-set time at which the oxygen level fall time is deemed excessive and a degradation signal is produced may be set as a function of the reinstatement fuel level and the value for the lower threshold, but typically, the pre-set time will be fixed at about 2 seconds±20%.

The oxygen sensor degradation signal produced if an excessive fall time is measured may cause a light or other warning device to turn on in order to alert the person operating the engine that the oxygen sensor needs service.

The performance evaluation method may be carried out on board a vehicle as it is travelling, rather than in a garage, for example.

Other objects, features and advantages of the present invention will be readily appreciated by the reader of this specification.

BRIEF DESCRIPTION OF THE DRAWINGS

The object and advantages claimed herein will be more readily understood by reading an example of an embodiment in which the invention is used to advantage with reference to the following drawings herein:

DESCRIPTION OF THE INVENTION

Figure 1:
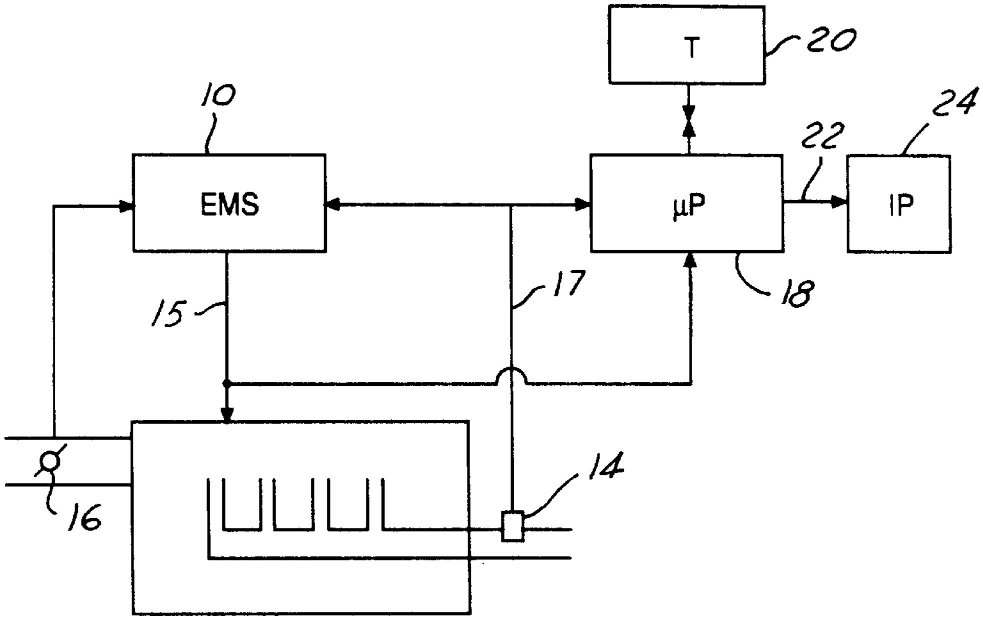
FIG. 1 is a block diagram for an example fuel controller according to the invention.

In FIG. 1, an engine management system (EMS) 10 controls the air and fuel input to an internal combustion engine 12 of a motor vehicle by issuing a command signal 15 to the engine 12. In order to optimise the ratio of the air-fuel mixture admitted to the engine 12, the engine management system 10 takes into account the oxygen content of the exhaust gas as sensed by an oxygen sensor 14. The internal combustion engine may be in a motor vehicle, and the oxygen sensor may be placed in the motor vehicle exhaust system, in order to monitor the exhaust gas emitted from the motor vehicle.

When an accelerator pedal controlling the engine throttle 16 is depressed or released, the command signal 15 passed to the engine 12 causes fuel to the engine to be respectively reinstated or cut off. Cutting off the fuel supply will normally result in a rapid rise in the oxygen content of the exhaust gas since the angular momentum of the engine or the momentum of a vehicle driven by the engine will keep the engine turning and drawing in air after the fuel has been cut off.

The command signal 15 from the engine management system 10 is also passed to a microprocessor ($\mu$P) 18 connected to the oxygen sensor 14 and a counter-timer (T) 20. (The microprocessor 18 could be integrated into the engine management system 10, but is shown here as a separate component).

If the oxygen level detected by the sensor 14 is above an upper threshold immediately before a command signal 15 for fuel reinstatement is issued by the engine management system 10, the microprocessor 18 is able to reset and cyclically increment the counter-timer 20 until the detected oxygen level reaches a lower threshold. The microprocessor 18 is able to read the counter-timer 20 so that if the time for the detected oxygen level to reach the lower threshold exceeds a pre-set time, the microprocessor 18 can send an oxygen sensor degradation signal 22 to a vehicle instrument panel (IP) 24 where for example a warning light will light up.

Although in FIG. 1 the oxygen sensor 14 is connected directly to the microprocessor 18, the oxygen sensor could alternatively be connected indirectly to the microprocessor via the engine management system 10.

Figure 2:
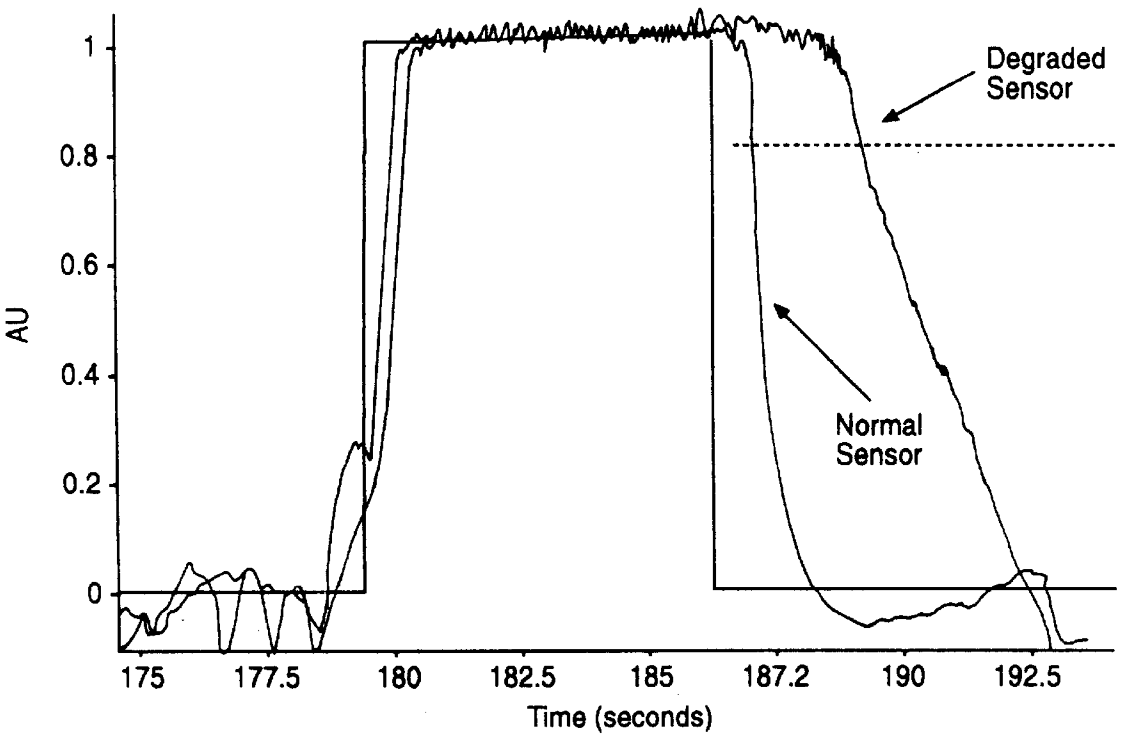
FIG. 2 is a graph illustrating how a normal oxygen sensor and a degraded oxygen sensor can be distinguished according to the invention.

FIG. 2 shows experimental traces in arbitrary units for the sensed oxygen content of the exhaust gas of the internal combustion engine 12, in this example a V8 4 liter engine, as a function of time when the oxygen sensor 14 is in the normal state and in the degraded state. Here time is measured in units of seconds.

The command signal 15 from the engine management system 10 governing the fuel supply varies with time so as to produce a trace as shown in FIG. 2. A high command signal 15 indicates that fuel to the engine 12 is cut off, whereas a low command signal indicates that fuel is being supplied to the engine 12. Initially, at T=175 seconds, the command signal 15 is low, so fuel is being supplied to the engine, and the oxygen content of the exhaust gas is low. This represents the steady state fuelling of the engine 12, when the accelerator pedal controlling the engine throttle 16 is depressed. When the accelerator pedal is released, the command signal 15 changes from low to high as indicated in FIG. 2 at about T=178 seconds, and fuel cut-off takes place. The oxygen levels detected by the degraded sensor and the normal sensor rise quickly to a common saturation value since only air is being drawn into the engine.

When the accelerator pedal is depressed again, the command signal 15 changes from high to low abruptly, in a step-wise fashion, and the oxygen levels detected by the degraded sensor and the normal sensor both drop, but at a different rate, the oxygen level sensed by the degraded sensor taking longer to drop that that sensed by the normal sensor.

The response time of the normal sensor and the degraded sensor can be compared from the time at which the sensed oxygen level drops below a lower threshold value, here about 80% of the maximum detected oxygen concentration as indicated by the dotted line in FIG. 2. The oxygen level sensed by the normal sensor reaches the lower threshold about 0.95 seconds after fuel reinstatement has been initiated, as measured from the negative edge of the command signal step. In contrast, with the degraded sensor the sensed oxygen level reaches the lower threshold about 2.65 seconds after fuel has been reinstated.

The time taken for the detected oxygen level to fall to the lower threshold is due to the fall time of the actual oxygen concentration and the response time of the oxygen sensor. Since the actual oxygen fall time in the traces for the normal sensor and the degraded sensor is expected to be similar, the difference in the detected fall times, here about 1.7 seconds, is due to the increased response time of the degraded sensor. The response time of a normal sensor, here a Universal Heated Exhaust Gas Oxygen sensor, is typically about 10 ms, a very short time on the time scale of FIG. 2, and about two orders of magnitude lower than the increase in response time of the degraded sensor. Although the difference in the response times of the two sensors could in principle be measured when the oxygen level is rising, just after fuel cut off, the difference is relatively small as can be seen from FIG. 2, making the measurement more difficult.

Figure 3:
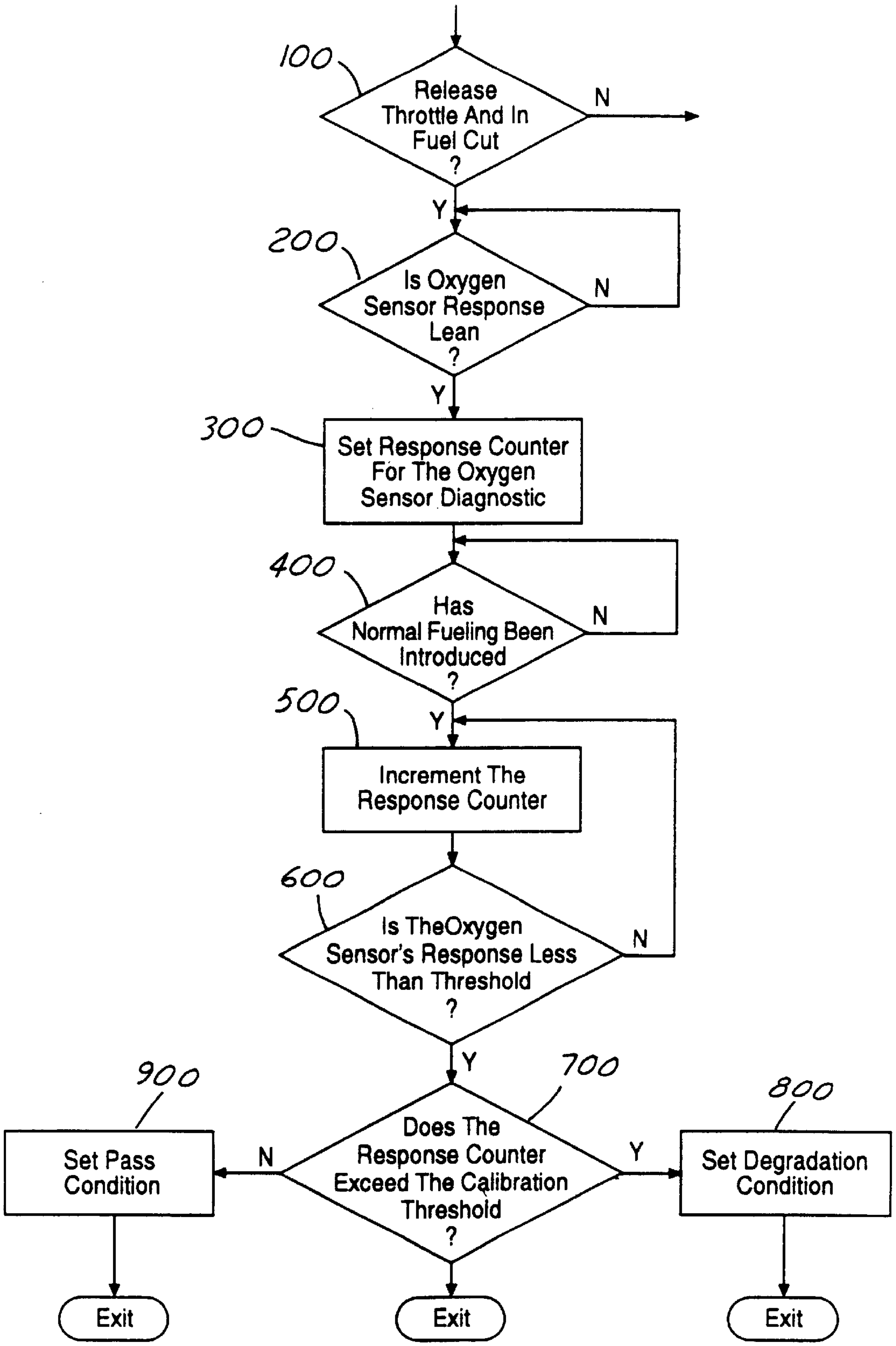
FIG. 3 is a flow diagram showing the steps of the performance evaluation method.

The performance evaluation procedure can be more clearly described with reference to FIG. 3, which is a flow diagram of the steps involved, carried out by the microprocessor 18.

First, in step 100 the microprocessor 18 waits until it receives a command signal 15 indicating that that the engine 12 is in fuel cut mode. The engine will be in fuel cut off mode after the accelerator pedal controlling the engine throttle 16 has been released (this is the situation at T=178 seconds in FIG. 2 when the command signal has risen to a high value). The procedure then continues to decision block 200. Before the performance evaluation procedure can continue, sufficient time must have elapsed for the fuel to be flushed out of the engine so that the oxygen sensor reaches saturation and produces a lean response (in FIG. 2 this occurs at approximately T=180 seconds). In step 200 a determination is made whether the oxygen sensor produces a lean response. If the answer to step 200 is NO, the procedure cycles until a YES answer is received. So when the microprocessor 18 has received a signal 17 from the oxygen sensor 14 indicating that the sensed oxygen level has saturated, the procedure continues to step 300 whereupon the microprocessor 18 sets to zero the response counter-timer 20 in preparation for the next step in the procedure.

Next, in step 400, a determination is made whether normal fuelling has been introduced. If the answer to step 400 is NO, the procedure cycles until a YES response is received. This happens when the engine management system 10 issues a command signal 15 that changes to low, indicating the onset of fuel reinstatement, which in FIG. 2 occurs at T=186 seconds. If the answer to step 400 is YES, the procedure continues to step 500 whereupon the microprocessor increments the counter-timer. Next, the procedure continues to step 600 whereupon a decision is made whether the detected oxygen concentration level is below the pre-set lower threshold. If the answer to step 600 is NO, the procedure returns to step 500, and the counter-timer is incremented again. If the answer to step 600 is YES, the procedure continues to step 700, whereupon a determination is made whether the counter-timer reading is above a predetermined calibration threshold. If the answer to step 700 is YES, a degradation condition is set, and the microprocessor 18 sends a degradation signal 22 to the vehicle instrument panel 24 that consequently displays a warning to show that the oxygen sensor is degraded. (The pre-set time reading above which the degradation signal 22 is sent is 2 seconds for the V8 4 liter engine 12 used in producing the graph of FIG. 2, but the pre-set time may be different with a different engine or if the sensor 14 is placed in a different position in the engine exhaust system). The driver of the vehicle is thereby informed that the oxygen sensor 14 requires attention, and can take the vehicle in for corrective action. If the answer to step 700 is NO, no degradation is detected.

Thus, according to the present invention, it is possible to accurately detect degradation of an oxygen sensor by comparing the time it takes for the oxygen sensor to switch from a rich reading to a lean reading and comparing it to a predetermined calibration threshold.

This concludes the description of the invention. The reading of it by those skilled in the art would bring to mind many alterations and modifications without departing from the spirit and the scope of the invention. Accordingly, it is intended that the scope of the invention is defined by the following claims.

What is claimed is:

1. A method for evaluating the performance of an oxygen sensor that detects an oxygen concentration level in an exhaust gas from an internal combustion engine, the method comprising:

- cutting off a fuel supply to the internal combustion engine and allowing the detected oxygen concentration level of the exhaust gas to rise;
- reinstating said fuel supply after the detected oxygen concentration level has risen above a pre-determined upper threshold;
- measuring a fall time for the detected oxygen concentration level to fall to a pre-determined lower threshold from the moment said fuel supply is reinstated; and
- producing an oxygen sensor degradation signal if said measured fall time exceeds a pre-set time.

2. The method as claimed in claim 1, wherein the internal combustion engine is in a motor vehicle, and the oxygen sensor is placed in the motor vehicle exhaust system, in order to monitor the exhaust gas emitted from the motor vehicle.

3. The method as claimed in claim 2, wherein said fuel supply is cut off by an engine management system when an accelerator pedal controlling said fuel supply is released.

4. The method as claimed in claim 3, wherein said fuel supply is reinstated by the engine management system when the accelerator pedal is depressed.

5. The method as claimed in claim 3, wherein said fall time for the detected oxygen concentration level to reach said predetermined lower threshold is measured from the moment the engine management system issues a command signal for fuel reinstatement.

6. The method as claimed in claim 5, wherein the engine management system provides a command signal for fuel reinstatement that comprises a single step.

7. The method as claimed in claim 6, further comprising measuring said fall time for the detected oxygen concentration level to reach said predetermined lower threshold by a counter-timer that is set to run by a microprocessor when the microprocessor senses a negative edge of a command signal for fuel reinstatement issued by the engine management system.

8. The method as claimed in claim 7, further comprising re-setting the counter-timer to zero by the microprocessor after said predetermined lower threshold has been reached.

9. The method as claimed in claim 8, further comprising fixing said pre-set time at 2 seconds ±20%.

10. The method as claimed in claim 1, wherein the oxygen sensor is used to determine when said predetermined upper threshold has been reached.

11. The method as claimed in claim 1, wherein said predetermined upper threshold is the oxygen concentration level at which the oxygen sensor saturates.

12. The method as claimed in claim 1, wherein said predetermined lower threshold is fixed at between 70% and 85% of said predetermined upper threshold oxygen concentration.

13. The method as claimed in claim 1, wherein said predetermined lower threshold is varied as a function of said reinstated fuel supply level.

14. The method as claimed in claim 1, further comprising setting said pre-set time as a function of a reinstatement fuel level and said predetermined lower threshold value.

15. The method as claimed in claim 14, further comprising turning a warning device on when said oxygen sensor degradation signal is produced.

16. The method as claimed in claim 15, wherein the performance evaluation method is carried out on board a vehicle as it is travelling.

17. A performance evaluating system for detecting a degradation in an oxygen sensor that detects an oxygen concentration level of an exhaust gas of an internal combustion engine, the performance evaluator comprising:

- means for cutting off a fuel supply to the internal combustion engine and allowing the detected oxygen concentration level of the exhaust gas to rise;
- means for reinstating a fuel supply after the detected oxygen concentration level has risen above a predetermined upper threshold;
- means for measuring a fall time from the moment said fuel supply is reinstated for the detected oxygen concentration level to fall to a pre-determined lower threshold; and
- means for producing an oxygen sensor degradation signal if said measured fall time exceeds a pre-set time.

18. A fault detector for detecting a fault in an oxygen sensor that senses the oxygen concentration of the exhaust gas of an internal combustion engine with an engine management system, the fault detector comprising: a microprocessor, responsive to signals from the engine management system and the oxygen sensor, such microprocessor having a counter-timer, wherein if the microprocessor receives a command signal from the engine management system indicating that fuel to the engine has been cut off, followed by a signal from the oxygen sensor indicating that the sensed oxygen level has reached an upper threshold, the microprocessor measures the elapsed time from the moment the engine management system issues a command for fuel reinstatement until the sensed oxygen has fallen to a lower threshold value, and if the elapsed time is greater than a pre-set time, to issue an oxygen sensor fault signal.

* * * * *